(12) United States Patent
Cameron et al.

(10) Patent No.: US 11,358,933 B2
(45) Date of Patent: Jun. 14, 2022

(54) COMPOUNDS AND METHODS FOR INHIBITING CYP26 ENZYMES

(71) Applicant: Queen's University at Kingston, Kingston (CA)

(72) Inventors: Donald Andrew Cameron, Kingston (CA); Martin Petkovich, Kingston (CA); Uttam Saha, Thornhill (CA)

(73) Assignee: Queen's University at Kingston, Kingston (CA)

( * ) Notice: Subject to any disclaimer, the term of this patent is extended or adjusted under 35 U.S.C. 154(b) by 0 days.

(21) Appl. No.: 17/084,071

(22) Filed: Oct. 29, 2020

(65) Prior Publication Data

US 2021/0107870 A1    Apr. 15, 2021

Related U.S. Application Data

(63) Continuation of application No. 16/771,255, filed as application No. PCT/CA2018/051582 on Dec. 12, 2018.

(60) Provisional application No. 62/597,619, filed on Dec. 12, 2017.

(51) Int. Cl.
| | |
|---|---|
| *C07D 209/08* | (2006.01) |
| *A61P 17/10* | (2006.01) |
| *C07C 59/84* | (2006.01) |
| *C07D 307/79* | (2006.01) |
| *C07D 311/58* | (2006.01) |
| *C07D 407/04* | (2006.01) |
| *C07F 5/02* | (2006.01) |
| *A61K 9/00* | (2006.01) |
| *A61K 45/06* | (2006.01) |

(52) U.S. Cl.
CPC ............ *C07D 209/08* (2013.01); *A61P 17/10* (2018.01); *C07C 59/84* (2013.01); *C07D 307/79* (2013.01); *C07D 311/58* (2013.01); *C07D 407/04* (2013.01); *C07F 5/025* (2013.01); *A61K 9/0014* (2013.01); *A61K 45/06* (2013.01)

(58) Field of Classification Search
CPC ............................... C07D 209/08; A61P 17/10
See application file for complete search history.

(56) References Cited

U.S. PATENT DOCUMENTS

| | | | |
|---|---|---|---|
| 4,478,842 A | 10/1984 | Renfroe | |
| 4,522,808 A | 6/1985 | Jacquet et al. | |
| 10,874,634 B2 * | 12/2020 | Cameron | ................. A61P 9/00 |

FOREIGN PATENT DOCUMENTS

| | | |
|---|---|---|
| AU | 3233599 A1 | 12/1999 |
| EP | 2141148 A1 | 1/2010 |
| WO | WO1998/27974 A1 | 7/1998 |
| WO | WO2001/49684 A1 | 7/2001 |
| WO | WO2011/050325 A1 | 4/2011 |
| WO | WO2013/019682 A1 | 2/2013 |
| WO | WO2015/186056 A1 | 12/2015 |
| WO | WO1997/21704 A1 | 6/2017 |

OTHER PUBLICATIONS

International Search Report and Written Opinion for corresponding International application No. PCT/CA2018/051582 filed on Dec. 12, 2018.

Tomoo, T., et al., "Design, Synthesis and Biological Evaluation of 3-(1-Aryl-1H-indol-5-yl)propanoic Acids as New Indole-Based Cytosolic Phospholipase AZα Inhibitors", Journal of Medicinal Chemistry, ACS, pp. 7244-7262. (2014).

* cited by examiner

*Primary Examiner* — Golam M Shameem
(74) *Attorney, Agent, or Firm* — Angela Lyon

(57) ABSTRACT

Compounds that are inhibitors of retinoic acid inducible P450 (CYP26) enzymes. The compounds have retinoid activity, are resistant to CYP26-mediated catabolism, act as inhibitors of CYP26B1, and are used for treating diseases that are responsive to retinoids.

9 Claims, 11 Drawing Sheets

COMPOUNDS AND METHODS FOR INHIBITING CYP26 ENZYMES

This application is a continuation of application Ser. No. 16/771,255, filed on Jun. 10, 2020, which is a national phase filing of International Application No. PCT/CA2018/051582, filed on Dec. 12, 2018, and claims the benefit of the filing date of U.S. Provisional Patent Application No. 62/597,619, filed on Dec. 12, 2017, the entire contents of which are incorporated herein by reference.

FIELD

The invention relates to compounds that inhibit certain cytochrome P450 enzymes (P450RAI), which are known as CYP26. It also relates to compounds that have retinoid-like activity.

BACKGROUND

Vitamin A metabolism gives rise to several active forms of retinoic acid (RA) which are involved in regulating gene expression during development, regeneration, and in the growth and differentiation of epithelial tissues. RA has been linked to apoptosis (i.e., programmed cell death) in a number of cell types, and has been shown to have anti-carcinogenic and anti-tumoral properties. Early studies of retinol deficiency indicated a correlation between vitamin A depletion and a higher incidence of cancer and increased susceptibility to chemical carcinogenesis. Several animal models have been used to demonstrate the effectiveness of retinoids in suppressing carcinogenesis in a variety of tissues including skin, mammary epithelia, oral cavity, aerodigestive tract, liver, bladder and prostate. These studies have led to the preventative use of retinoids in the treatment of premalignant lesions, as well as in the prevention of secondary tumours (e.g., prevention of recurrence of non-small cell lung carcinomas and basal cell carcinomas). RA itself has been found to be useful therapeutically, notably in the treatment of cancers. Studies have shown that cytochrome P450 inhibitors that block RA metabolism, result in increased levels of RA, which may be useful therapeutic agents in the treatment of cancer (Wouters W., et al., *Cancer Res* (1992) 52:2841-6). Thus RA metabolizing cytochrome P450s may be useful targets for the treatment of a number of different types of cancer.

SUMMARY

In one aspect, the invention provides a compound of formula:

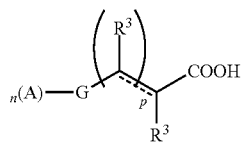

where A is a substituted or unsubstituted hydrophobic moiety, G is a moiety that comprises a substituted or unsubstituted heteroaryl group, or a moiety that comprises a substituted or unsubstituted aryl group and at least one heteroatom,
$R^3$ is independently H, halo, or a substituted or unsubstituted $C_1$-$C_4$,
a dotted line is a bond that may be present or absent, n is 1 or 2, p is zero to 3, wherein a substituent is independently alkyl, aryl, halo, nitro, hydroxyl, amino, thiol, alkoxyl, amido, amide, boryl, carboxyl, alkenyl, allyl, cyano, substituted alkyl (e.g., alkylamino, halogenated alkyl), unsubstituted alkyl, or a combination thereof.

In one embodiment, the invention provides a compound of Formula (1)

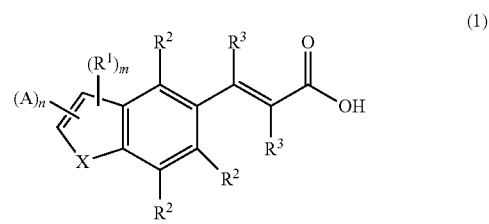

where A is a substituted or unsubstituted hydrophobic moiety, n is 1 or 2, $R^1$, $R^2$, and $R^3$ are independently H or substituted or unsubstituted $C_1$-$C_4$, m is zero or 1, wherein a substituent is independently alkyl, aryl, halo, nitro, hydroxyl, amino, thiol, alkoxyl, amido, amide, carboxyl, alkenyl, allyl, cyano, substituted alkyl (e.g., alkylamino, halogenated alkyl), or unsubstituted alkyl. In one embodiment, A is an aromatic moiety that is substituted or unsubstituted and X is a heteroatom. In one embodiment, the compound is a compound of formula (1a)

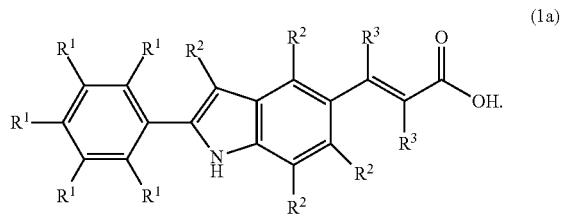

In one embodiment, the compound is Compound 025, 026, 027, 028, 029, 030, 031, 032, 033 or 034 of Table 1. In one aspect, the invention provides compound 026 of Table 1.

In one aspect, the invention provides a method of treating a disease or condition in a mammal, comprising administering an inhibitor of the breakdown of RA, comprising a compound of the above formulas. In one embodiment, the disease or condition is a skin disease or skin condition. In one embodiment, the skin disease or skin condition is actinic keratosis, arsenic keratosis, inflammatory and non-inflammatory acne, psoriasis, ichthyosis and other keratinization, hyperproliferative disorders of the skin, eczema, atopic dermatitis, Darriers disease, lichen planus, glucocorticoid damage, or steroid atrophy. In one embodiment, the compound is applied as a topical antimicrobial, a skin anti pigmentation agent, to treat and reverse the effects of age and photo damage to the skin. In one embodiment, the method of treating a disease or condition in a mammal, further comprises preventing cancerous or precancerous conditions. In one embodiment of this aspect, the condition is premalignant or malignant hyperproliferative diseases, cancer of the breast, skin, prostate, cervix, uterus, colon, bladder, esophagus, stomach, lung, larynx, oral cavity, blood, lymphatic system, metaplasias, dysplasias, neoplasias, leukoplasias, or papillomas of the mucous membranes, or Kaposi's sarcoma. In one embodiment, the compound is useful to treat diseases of the eye comprising proliferative vitreoretinopathy (PVR), retinal detachment, dry eye, corneopathies. In one embodiment, the compound is useful to treat cardiovascular disease. In one embodiment, the cardiovascular disease comprises diseases associated with lipid metabolism, dyslipidemias, prevention of post-angioplasty restenosis. In one embodiment, the compound is useful as an agent to increase the level of circulating tissue plasminogen activator (TPA), or to treat or prevent conditions and diseases associated with human papilloma virus (HPV), inflammatory disease such as pulmonary fibrosis, ileitis, colitis and Crohn's disease, neurodegenerative disease such as Alzheimer's disease, Parkinson's disease, stroke, improper pituitary function including improper production of growth hormone, modulation of apoptosis including both the induction of apoptosis, and inhibition of T-cell activated apoptosis, restoration of hair growth, diseases associated with the immune system, modulation of organ transplant rejection, facilitation of wound healing. In one embodiment, the compound is useful in treating type II non-insulin dependent diabetes mellitus, disorders of ectopic bone formation, or muscle tissue calcification. In one embodiment, a medicament is administered as a powder, spray, pill, tablet, syrup, elixir, solution or suspension capable of being administered by injection, suppository, extended release formulation for deposit under the skin or intramuscular injection. In one embodiment of this aspect, a compound is included in a medicament for topical application in a formulation comprising between 0.01 milligrams and 1 mg per mL of the compound. In one embodiment, a compound is included in a medicament for systemic administration in a formulation comprising between 0.01 and 5 mg per kg body weight per day. In one embodiment, the compound is given in combination with a retinoid or a retinoid precursor selected from retinol, retinaldehyde, RA, or other natural or synthetic retinoids. In one embodiment, the combination is provided in a tablet, capsule, injectable, or topical formulation. In one embodiment of the aspects described herein, the compound is Compound 026 of Table 1. In one embodiment, the compound is 025, 026, 027, 028, 029, 030, 031, 032, 033, or 034 of Table 1.

In one aspect, the invention provides a pharmaceutical composition comprising a compound as described herein. In one embodiment, the pharmaceutical composition further comprises an excipient. In one embodiment, the compound is 025, 026, 027, 028, 029, 030, 031, 032, 033, or 034 of Table 1.

BRIEF DESCRIPTION OF THE DRAWINGS

For a better understanding of the invention and to show more clearly how it may be carried into effect, reference will now be made, by way of example, to the accompanying drawings, wherein.

DETAILED DESCRIPTION OF EMBODIMENTS

Definitions

Figure 1:
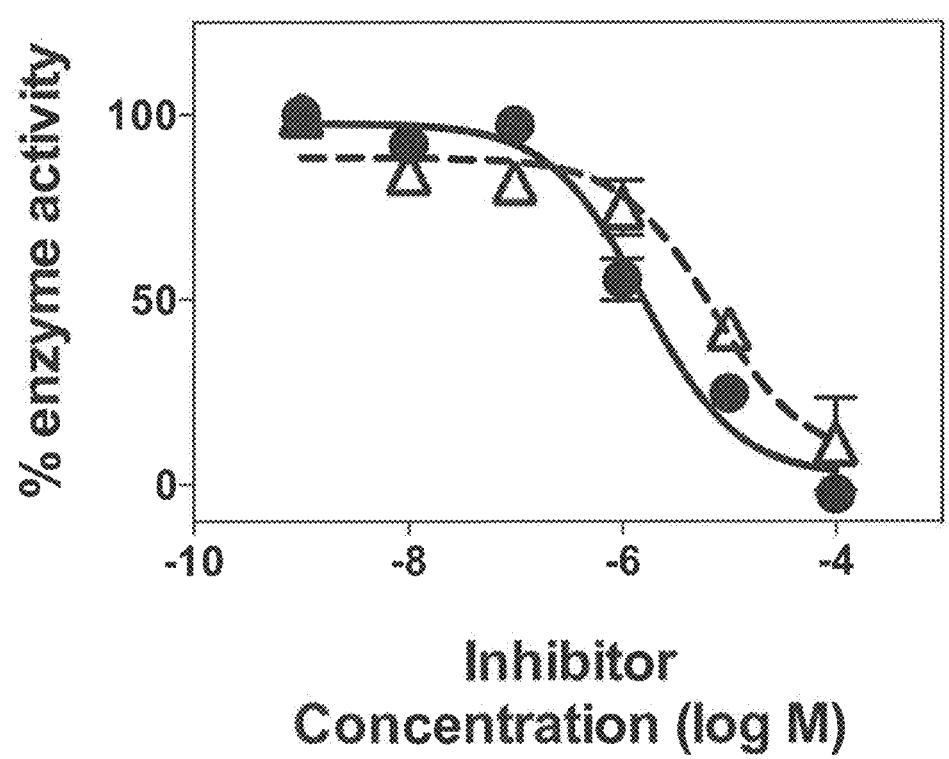
FIG. 1 shows a plot of activity of the CYP26A1 enzyme in the presence of increasing concentrations of compound 026 (white triangles) versus ketoconazole (black triangles).

As used herein, the term "RA" refers to retinoic acid.

As used herein, the term "A" refers to a hydrophobic moiety, such as a $C_4$-$C_{50}$ moiety, which may be aromatic, non-aromatic, cyclic, non-cyclic, or any combination thereof, and is substituted or unsubstituted. Typical hydrophobic moieties may include phenyl, heteroaryl, or aliphatic moieties.

As used herein, the term "MEM" refers to Minimum Essential Medium (available from Sigma-Aldrich, Oakville, Canada).

As used herein, the term "MEM-α" refers to Minimum Essential Medium, a modification (available from Thermofisher Scientific, Ottawa, Canada).

As used herein, the term "IMDM" refers to Iscove's Modified Dulbecco's Medium (available from Sigma Aldrich, Oakville, Canada).

As used herein, the term "RMPI-1640" refers to Roswell Park Memorial Institute 1640 medium (available from Thermofisher Scientific, Ottawa, Canada).

As used herein, the term "APL" refers to acute promyelocytic leukemia.

As used herein, the term "AML" refers to acute myeloid leukemia.

As used herein, the term "FBS" refers to fetal bovine serum (available from Sigma-Aldrich, Oakville, Canada).

As used herein, the term "QPCR" refers to quantitative polymerase chain reaction.

As used herein, the term "DMSO" refers to dimethylsulphoxide.

As used herein, the term "CYP26" refers to a subfamily of cytochrome P450 enzymes which are specific in the metabolism of retinoic acid.

As used herein, the term "DPM" refers to disintegrations per minute.

As used herein, the term RARB refers to the retinoic acid receptor beta.

As used herein, the term Crabp2 refers to the cellular RA binding protein 2.

As used herein, the term "FACS" refers to fluorescence activated cell sorting.

As used herein, the term "MFI" refers to median fluorescence intensity.

As used herein, the term "CD11b" refers to the cluster of differentiation molecule 11b, which is also known as macrophage-1 antigen (Mac-1), integrin alpha M (ITGAM), or complement receptor 3 (CR3).

As used herein, the term "FLT3" refers to the FMS-related tyrosine kinase 3.

As used herein, the term "CD34" refers to cluster of differentiation molecule 34.

As used herein, the term "CD38" refers to cluster of differentiation molecule 38, which is also known as cyclic ADP ribose hydrolase.

As used herein, the term "PE" refers to fluorophore phycoerythrin.

As used herein, the term "FITC" refers to the fluorophore fluorescein isothiocyanate.

As used herein, the term "IL-3" refers to interleukin 3.

As used herein the term "LSC" refers to leukemic stem cell.

As used herein, the term "CFU" refers to colony forming unit.

As used herein, the term "MDS" refers to myelodysplastic syndrome.

As used herein, the term "PMM2" refers to the phosphomannomutase 2 gene.

As used herein, the term "Bglap" refers to the bone caroboxyglutamic acid-containing protein gene, also known as osteocalcin.

As used herein, the term "Ibsp" refers to the Integrin binding sialoprotein gene, which is also known as bone sialoprotein, or BSP.

As used herein, the term "CM" refers to control growth medium.

As used herein, the term "OM" refers to osteogenic medium.

As used herein, the term "IHC" refers to immunohistochemistry.

As used herein, the term "BCC" refers to basal cell carcinoma.

As used herein, the term "Smo" refers to smoothened.

As used herein, the term "unsubstituted" refers to any open valence of an atom being occupied by hydrogen. Also, if an occupant of an open valence position on an atom is not specified then it is hydrogen.

EMBODIMENTS

Several compounds having retinoid-like activity are marketed under appropriate regulatory approvals in the US and elsewhere as medications for the treatment of several disease that are responsive to retinoids. Retinoic acid (RA) itself is a natural product, biosynthesized and present in a multitude of human and mammalian tissues and is known to play an important role in the regulation of gene expression, tissue differentiation and maintenance, and other important biological processes in mammals including humans. A natural catabolic pathway exists in mammals, including in humans, of natural RA includes a hydroxylation step catalyzed by the CYP26 family of enzymes, including CYP26A1 and CYP26B1. Several inhibitors of CYP26A1 have been synthesized or discovered previously including liarazole, ketoconazole, and R116010. Administration to mammals of inhibitors of CYP26 results in significant increase of RA levels. Treatment with CYP26 inhibitors (e.g., liarazole) has been shown to have effects similar to treatment by retinoids, for example amelioration of psoriasis.

Embodiments of the present invention provide compounds that act as inhibitors of CYP26B1. Accordingly, such compounds have the potential to provide therapeutic benefit in the treatment of, or prevention of, diseases that respond to retinoids or that are controlled by natural RA. The perceived mode of action of these compounds is that by inhibiting the enzyme CYP26B1 that catabolizes natural RA, endogenous levels of RA are elevated to a level where desired therapeutic benefits are attained.

Broadly speaking, such compounds that act as inhibitors of CYP26B1 have three moieties connected to one another in the structure A-spacer-COOH. That is, such compounds have a hydrophobic moiety ("A"), a carboxylic acid moiety ("COOH"), and a spacer moiety ("spacer") that is bound to A at its first end, and is bound to COOH at its second end. Accordingly, the spacer is so named because it keeps A and COOH separated from one another, and the length of the spacer moiety determines the distance between A and COOH. In one embodiment, the spacer may be cyclic, linear, or a combination thereof. Both A and the spacer may be substituted or unsubstituted. In certain embodiments, the spacer comprises an aryl group. In other embodiments, the spacer comprises a non-aromatic cyclic moiety. In certain embodiments, the spacer is aliphatic and non-cyclic.

In one embodiment, such inhibitory compounds have a structural formulae as shown below

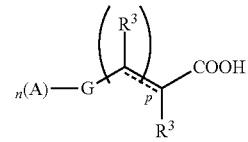

where A is a substituted or unsubstituted hydrophobic moiety,

G is a moiety that comprises a substituted or unsubstituted heteroaryl group, or a moiety that comprises a substituted or unsubstituted aryl group and at least one heteroatom;

$R^3$ is independently H, halo, or a substituted or unsubstituted $C_1$-$C_4$, a dotted line is a bond that may be present or absent;

n is 1 or 2, p is zero to 3, wherein a substituent is independently alkyl, aryl, halo, nitro, hydroxyl, amino, thiol, alkoxyl, amido, amide, boryl, carboxyl, alkenyl, allyl, cyano, substituted alkyl (e.g., alkylamino, halogenated alkyl), unsubstituted alkyl, or a combination thereof.

On one embodiment of the above formula, G comprises a fused aromatic ring system that includes at least one heteroatom. In one embodiment, such inhibitory compounds have a structural formulae as shown in Figure (1):

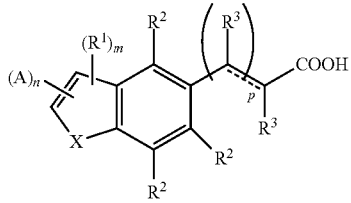
(1)

where A is a substituted or unsubstituted hydrophobic moiety, $R^1$, $R^2$, and $R^3$ are independently H, halo, or a substituted or unsubstituted $C_1$-$C_4$, a dotted line is a bond that may be present or absent;

X is a heteroatom (e.g., N, O, S)

n is 1 or 2, m is zero or 1, and p is zero to 3, wherein a substituent is independently alkyl, aryl, halo, nitro, hydroxyl, amino, thiol, alkoxyl, amido, amide, carboxyl, boryl, alkenyl, allyl, cyano, substituted alkyl (e.g., alkylamino, halogenated alkyl), unsubstituted alkyl, or a combination thereof.

Such inhibitory compounds are useful for prevention or treatment of diseases or conditions in mammals, including humans. Such diseases and conditions are prevented, treated, ameliorated, or disease onset is delayed by the administration of retinoid compounds or by the organism's naturally occurring RA. Since these compounds act as inhibitors of breakdown of RA, embodiments of the invention also relate to use of these compounds in conjunction with RA or other retinoids.

In one embodiment of Formula (1), A is an aromatic moiety that is substituted or unsubstituted as shown in formula (1a):

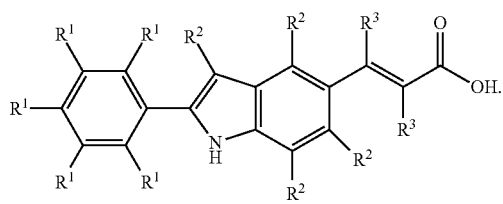
(1a)

Structural formulae of this and other compounds of Formula (1) are shown in Table 1. In one embodiment of compounds of Formulas (1) and (1a), the compound is compound 026:

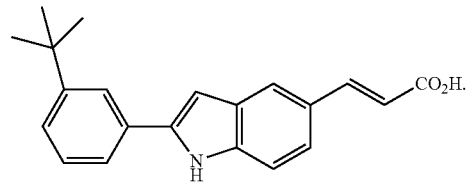
026

Figure 2:
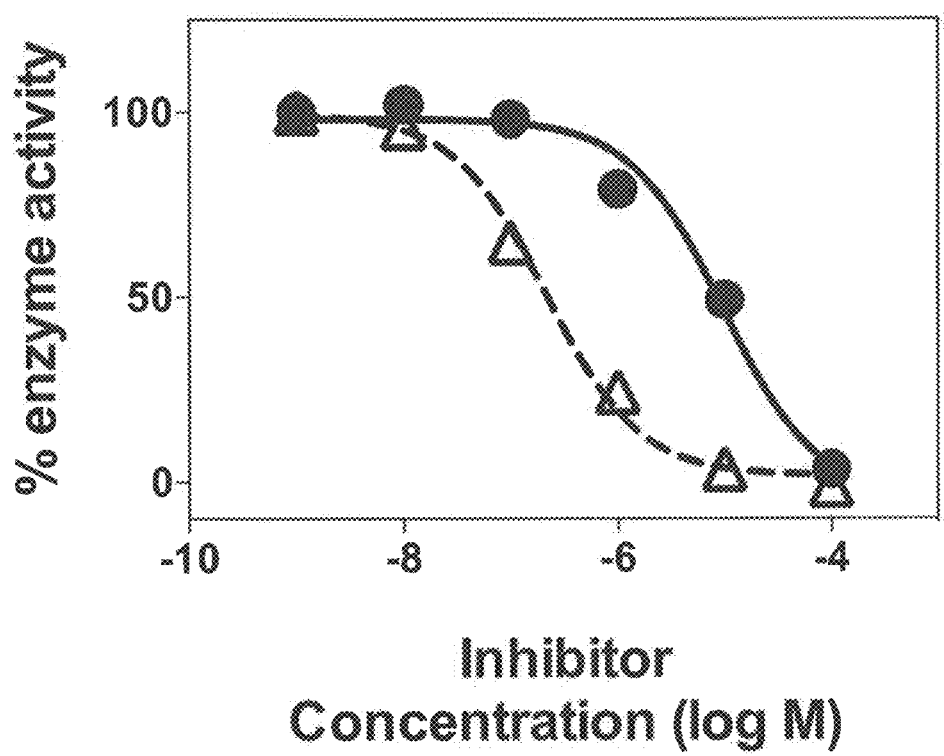
FIG. 2 shows a plot of activity of the CYP26B1 enzyme in the presence of increasing concentrations of compound 026 (white triangles) versus ketoconazole (black triangles).

In studies described herein, compound 026 was shown to be highly selective towards CYP26B1, with an $IC_{50}$ of 0.2 µM compared with 7 µM against CYP26A1 (see Table 2) in a HeLa cell-based assay (described below). FIG. 1 shows the inhibitory activity of compound 026 towards CYP26A1 as compared to ketoconazole. FIG. 2 shows inhibitory activity of compound 026 towards CYP26B1. Although this compound is comparable to ketoconazole with respect to CYP26A1 inhibition, FIG. 2 shows dramatically increased inhibition of CYP26B1 enzyme activity compared with ketoconazole. Importantly, this compound did not show agonist activity in the luciferase reporter transactivation experiment, indicating that it does not directly activate the RA signaling pathway. However, co-treatment of MCF-7 cells with 0.1 µM RA plus 1 µM compound 026 enhanced RA target gene transcription, and prolonged this response to at least 72 hours, indicating the desired mechanism of action.

Figure 4:
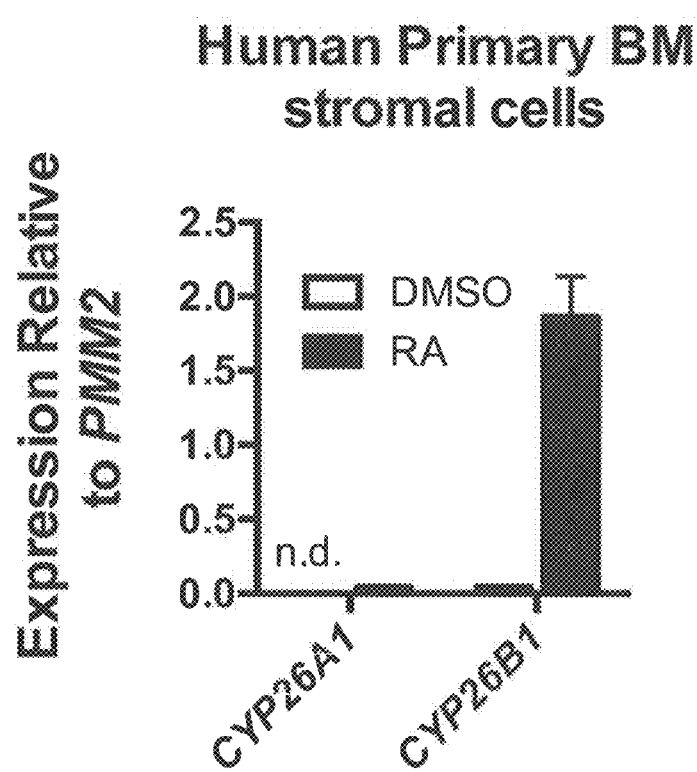
FIG. 4 shows a bar graph of QPCR analysis of CYP26 enzyme expression in primary human bone marrow stromal cells treated with vehicle (DMSO, white bars) or 1 µM RA (black bars) for 24 hours.
Figure 5:
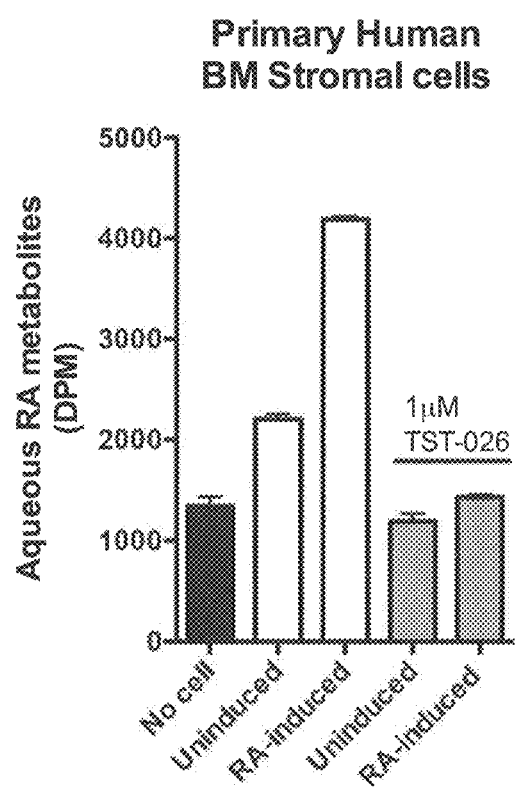
FIG. 5 shows a bar graph of RA metabolism by primary human bone marrow stromal cells pre-treated with vehicle (DMSO, uninduced) or 1 µM RA (RA-induced) for 24 hours, in the presence of either vehicle (DMSO, white bars) or 1 µM compound 026 (gray bars), as compared to culture media alone (black bar).

Human leukemic stem cells (LSCs) reside inside bone marrow and have been shown to persist during chemotherapy. They are thought to be responsible for disease relapse after initial remission. Some acute myeloid leukemias (AMLs) do not respond well to retinoid therapy, unlike APL. One suggested reason for this is localized metabolism of RA in the bone marrow by the activity of CYP26 enzymes. CYP26B1 was found to be highly expressed in cultured primary human bone marrow stromal cells compared to CYP26A1, which was undetectable (FIG. 4), suggesting that this isoform is largely responsible for the observed RA metabolism. Moreover, CYP26B1 expression, unlike CYP26A1, was also highly induced by treatment with RA (FIG. 4). Co-treatment of human bone marrow stromal cells with the CYP26B1-selective compound 026 greatly enhanced and prolonged expression of RA target genes in primary human bone marrow cells in response to RA, indicating that this compound can enhance RA signaling in bone marrow in culture. Furthermore, compound 026 efficiently blocked both basal and RA-induced RA metabolism in human bone marrow cells (FIG. 5) in a dose-dependent manner. Consistent with results from human bone marrow stromal cells, the mouse OP9 bone marrow stromal cell line, which is used extensively to support the long-term culture of human hematopoietic cells, displayed similar results with respect to Cyp26 enzyme expression and activity of compound 026; mouse Cyp26b1 is expressed much higher than Cyp26a1 In OP9 cells, as was also highly induced by 1 µM RA. Moreover, compound 026 efficiently blocked basal and RA-induced RA metabolism on OP9 cells in a similar manner to human cells.

CYP26B1 was also found to be expressed in bone marrow stromal elements in primary human bone marrow samples. CYP26B1 antibody immunohistochemical (IHC) staining was detected in megakaryocytes, endothelial cells, perivascular cells, and fibroblastic cells, all of which are known to be important components of the stem cell niche in bone marrow. Bone marrow samples from patients with increased number of megakaryocytes (chronic myeloid leukemia with increased megakaryocytes, and essential thrombocythemia) displayed increased staining with CYP26B1 antibody, including in platelets. Inhibition of CYP26B1 therefore could be used in disorders related to megakaryocytes such as platelet production, and clotting and bleeding disorders as well as modification of wound healing processes.

Figure 6:
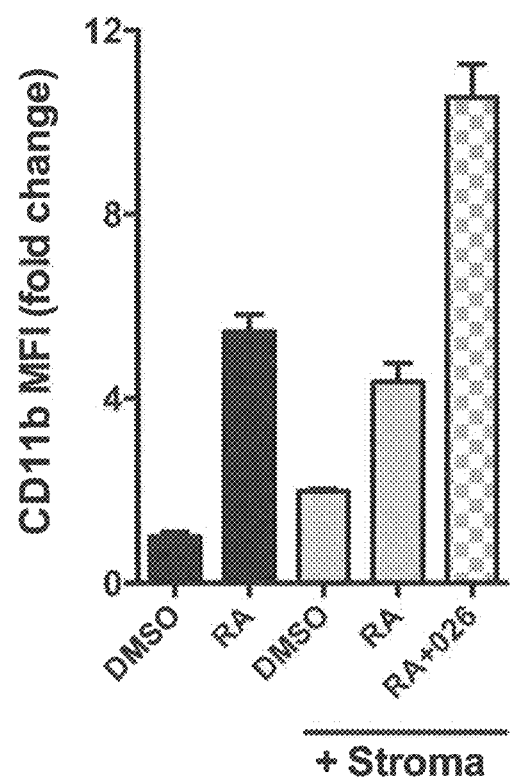
FIG. 6 shows a bar graph of FACS analysis of the fold change in PE-CD11b MFI of human AML THP-1 cells cultured in the presence or absence of mouse OP9 stromal cells, and treated with vehicle (DMSO), 0.1 µM RA, or 0.1 µM RA plus 1 µM compound 026 for 72 hours.

To test the ability of CYP26B1 inhibition to sensitize leukemic cells to the effects of RA, co-cultures of OP9 stromal cells and human AML cells were established. CD11b is a cell surface marker present on the surface of myeloid cells, and is indicative of myeloid differentiation. RA significantly increases expression of the CD11b marker on the surface of THP-1 cells as determined by MFI of PE-CD11b antibody stained cells (FIG. 6). Treatment of THP-1 cells with RA (0.1 µM) in combination with compound 026 (1 µM) in the presence of OP9 stroma greatly enhanced CD11b MFI (FIG. 6). Furthermore, compound 026 sensitized THP-1 cells to low doses of RA in the presence of stroma, suggesting that RA metabolism by bone marrow stroma can help to protect AML cells from exposure to RA and subsequent differentiation, and that chemical inhibition of CYP26B1 can block this effect. Consistent with these data, colony forming ability (indicative of LSC activity) was reduced in THP-1 cells by exposure to RA, and this was blocked by culture with stromal cells. The addition of compound 026 rescued the effects of RA and decreased colony forming units.

Figure 7:
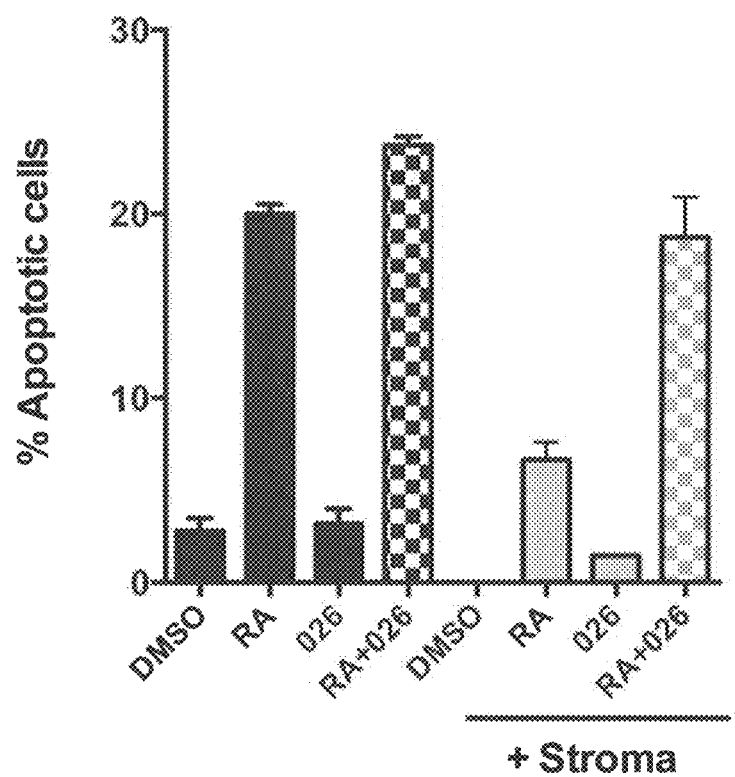
FIG. 7 shows a bar graph of FACS analysis of the percentage of apoptotic (FITC-Annexin V positive) MV4-11 cells grown in the presence or absence of mouse OP9 cells and treated with vehicle (DMSO), 0.1 µM RA, 1 µM compound 026, or 0.1 µM RA plus 1 µM 026 for 48 hours.

MV4-11 cells are another human AML cell line containing internal tandem duplication of the FLT3 gene that is common in human AML. RA increased the percentage of CD11b$^+$ MV4-11 cells, and the presence of stroma blocked this effect. Compound 026 rescued RA-induced differentiation in the presence of stroma. MV4-11 cells also undergo apoptosis in response to RA, and this effect was similarly blocked by the presence of stromal cells, and rescued by the addition of compound 026 (FIG. 7), indicating that RA metabolism can also protect AML blasts from apoptosis in response to RA.

Figure 8:
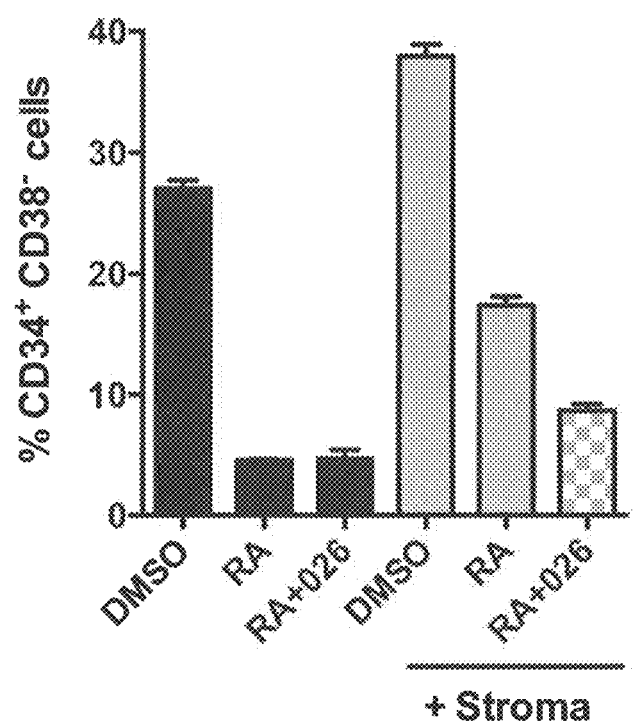
FIG. 8 shows a bar graph of FACS analysis of the percentage of FITC-CD34 positive/PE-CD38 negative LSCs in kasumi-1 human AML cells grown in the presence or absence of mouse OP9 cells and treated with vehicle (DMSO), 1 µM RA, or 1 µM RA plus 1 µM RA for 72 hours.

LSCs have been shown to be enriched in a fraction of AML cells that are positive for the hematopoietic progenitor marker CD34 and negative for the differentiation marker CD38. Kasumi-1 AML cells have a relatively high proportion of these CD34$^+$CD38$^-$ LSCs that can be readily detected by flow cytometry. Treatment with 1 µM RA significantly reduced the number of these cells, but the presence of OP9 bone marrow stroma mostly blocked this effect (FIG. 8). Addition of compound 026 restored the ability of RA to reduce the number of CD34$^+$CD38$^-$ cells (FIG. 8). Similar results were obtained using MDSL cells; a cell line derived from a patient with myelodysplastic syndrome (MDS), a condition that often leads to AML.

Figure 9:
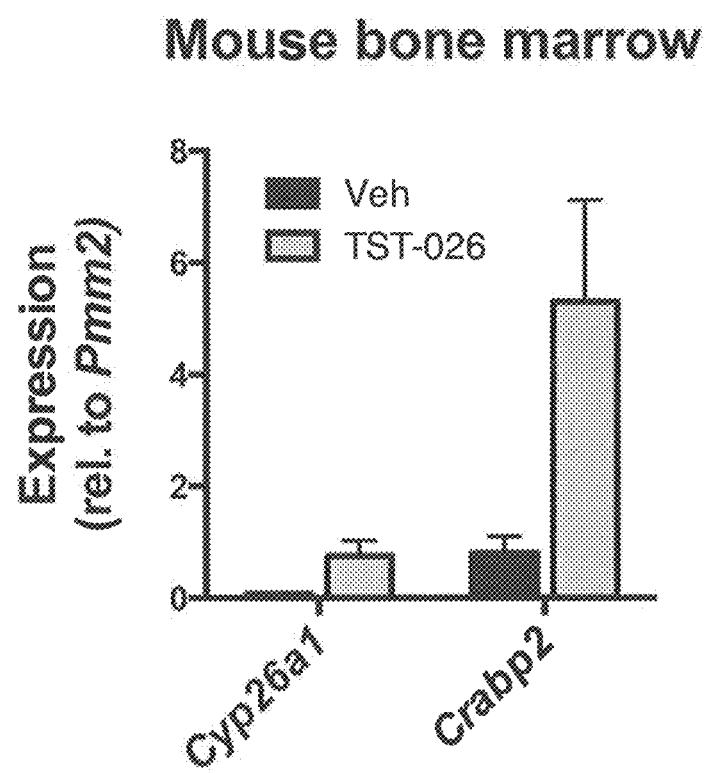
FIG. 9 shows a bar graph of QPCR analysis of RA target gene (Cyp26a1, and Crabp2) expression in bone marrow mononuclear cells isolated from mice given intravenous doses of vehicle (saline/0.1% DMSO, black bars) or compound 026 (40 µg/kg, gray bars).

To test the ability of CYP26B1 inhibitor compounds to alter exposure of hematopoietic cells to RA within the bone marrow in vivo, mice were given intravenous injections of either vehicle (0.9% saline/0.1% DMSO) or compound 026 once per day for two consecutive days. The next day, bone marrow mononuclear cells were harvested from mice to examine expression of RA target genes. Expression of Cyp26a1 and Crabp2 were both induced in 026 injected mice as compared with vehicle injected mice (FIG. 9) indicating that these cells were exposed to RA upon treatment with the compound.

RA is also known to impact bone cell differentiation at different stages of development, and Cyp26b1 is required for proper skeletal development. Therefore, we also tested whether CYP26B1 inhibition could block the formation of differentiated bone cells (osteoblasts). The MC3T3-E1 cell line is a pre-osteoblast line derived from mouse calvaria that undergoes osteogenic differentiation when cultured in osteogenic medium.

Figure 10:
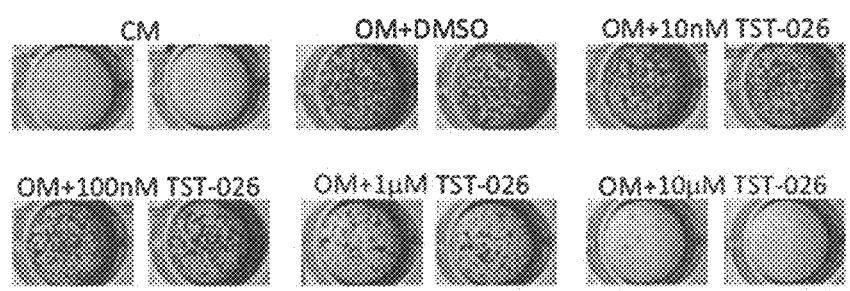
FIG. 10 shows alizarin red stained MC3T3 cells grown in control medium (CM) or osteogenic medium (OM) for 21 days in the presence of vehicle (DMSO), or increasing concentrations of compound 026.

This line can be used to study factors involved in bone cell differentiation and for screening potential inhibitors of osteoblast formation. MC3T3 cells were found to express high levels of Cyp26b1 as compared to Cyp26a1, and RA greatly induced expression of Cyp26b1 but not Cyp26a1. Moreover, MC3T3 cells readily metabolize RA, and this activity in increase upon pre-treatment with 1 µM RA for 24 hours. Compound 026 was found to block basal as well as RA-induced RA metabolism in these cells in a dose-dependent manner. Osteoblast differentiation is characterized by expression of osteoblast specific genes as well as the presence of a highly calcified extracellular matrix, which can be detected by the stain alizarin red. MC3T3 cells grown in osteogenic medium (OM) for 21 days formed a calcified matrix, as revealed by alizarin red staining (FIG. 10), and this was reduced by the presence of compound 026 in a dose-dependent manner. Marker gene expression analysis revealed that osteoblast gene Bglap, and Ibsp were highly expressed in vehicle (DMSO) treated cells grown in OM, while 10 µM compound 026 blocked their expression, suggesting an impairment of osteoblast formation in response to OM. Furthermore, treatment with a low dose of RA (10 nmol) which does not block osteogenic differentiation alone, was effective in the presence of 1 µM compound 026 in suppressing Bglap and Ibsp expression. To confirm increased RA signaling in this context, expression of the Cyp26b1 gene was also measured, since it is highly induced by RA in these cells. MC3T3 cells treated with compound 026 showed dramatic upregulation of Cyp26b1 compared with controls, indicating an increase in RA exposure.

Figure 11:
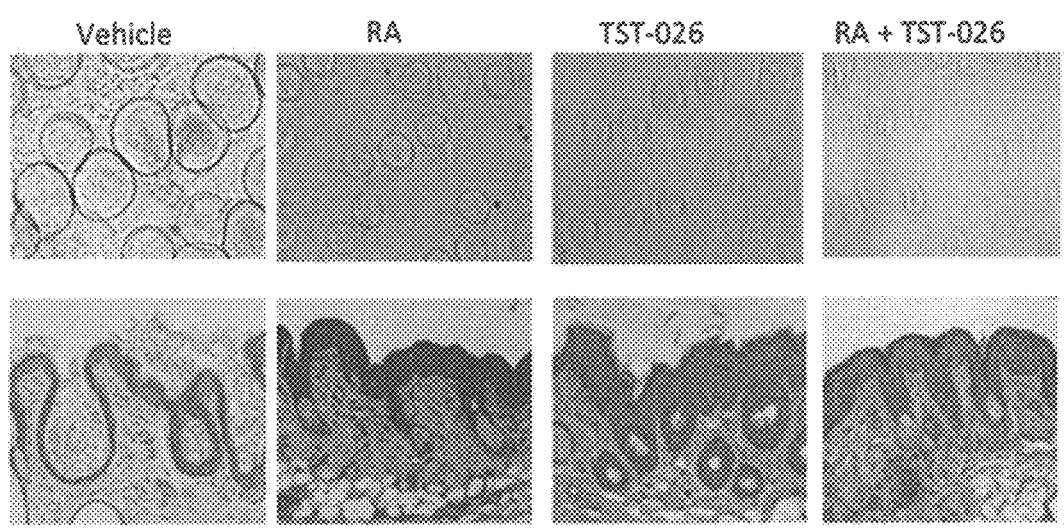
FIG. 11 shows photographs of epidermal sheet preparations (top panels) and skin histological sections (stained with hematoxylin and eosin, bottom panels) from rhino mice treated topically with vehicle, 10 nmol RA, 2 µmol 026, or 10 nmol RA plus 2 µmol 026 for 2 weeks (photographs are 200× magnification).

Retinoids are widely used in dermatological contexts and have been particularly effective in treating acne, although they also carry significant toxic effects when administered systemically. We used the rhino mouse model of acne as a means to assess the potential efficacy of CYP26B1 inhibition as an alternative treatment. 6-8 week old hairless rhino mutant mice were treated topically 5 times per week for two consecutive weeks with vehicle (acetone/10% DMSO), RA (10 nmol), compound 026 (2 umol) or the combination of RA and 026. Vehicle treated mice have large keratin filled utriculi in the epidermis and dermis, and these can be seen in epidermal sheets preparations and well as histological sections (FIG. 11, left-most panels). Treatment with RA causes a reduction in the size of these utriculi, and a thickening of the epidermis (FIG. 11). This effect was also seen upon treatment with compound 026 alone, or in combination with RA, indicating that cutaneous chemical inhibition of CYP26B1 may be sufficient to reduce acne lesions in epidermis.

Human skin samples were also analyzed for the presence of CYP26B1 by IHC. Hair follicles and sebaceous glands showed positive staining. These experiments also revealed strong CYP26B1 expression in basal cell carcinoma (BCC) tumour cells. These results indicate that CYP26B1 inhibition might also be useful in treating BCC patients. Patients with advanced BCC are often treated with drugs that inhibit the Smoothened (Smo) protein, such as Vismodegib, which results in tumour shrinkage. Patients must indefinitely take these drugs however, since tumours can quickly relapse after discontinuation. Recent work in mice showed that treating residual vismodegib-resistant BCC cells with RA could sensitize them to Smo inhibition and eradicate tumours.

Thus, inhibition of CYP26B1 in combination with Smo inhibition might be a useful therapeutic strategy in BCC.

It is noted that retinoids are useful in the treatment of skin diseases including but not limited to: actinic keratosis, arsenic keratosis, inflammatory and non-inflammatory acne, psoriasis, ichthyosis and other keratinization and hyperproliferative disorders of the skin, eczema, atopic dermatitis, Darriers disease, lichen planus, prevention and reversal of glucocorticoid damage (steroid atrophy). Such compounds can be applied as a topical antimicrobial, as skin anti pigmentation agents, and to treat and reverse the effects of age and photo damage to the skin.

The retinoids are also useful for the treatment or prevention of cancerous and precancerous conditions including premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplasias, and papillomas of the mucous membranes and in the treatment of Kaposi's sarcoma. In addition, retinoid compounds can be used to treat diseases of the eye including, but not limited to, proliferative vitreoretinopathy (PVR), retinal detachment and dry eye and other corneopathies, as well as in the treatment and prevention of various cardiovascular diseases including, but not limited to, diseases associated with lipid metabolism such as dyslipidemias, prevention of post-angioplasty restenosis, and as an agent to increase the level of circulating tissue plasminogen activator (TPA). Other uses for retinoid compounds include the treatment and prevention of conditions and diseases associated with human papilloma virus (HPV) including warts and genital warts, various inflammatory diseases such as pulmonary fibrosis, ileitis, colitis and Crohn's disease, neurodegenerative disease such as Alzheimer's disease and Parkinson's disease and stroke, improper pituitary function including improper production of growth hormone, modulation of apoptosis including both the induction of apoptosis, and inhibition of T-cell activated apoptosis, restoration of hair growth, including combination therapies with the present compounds and other agents such as Minoxidil, diseases associated with the immune system including the use of the current compounds as immunosuppressants and immunostimulants, modulation of organ transplant rejection and facilitation of wound healing including modulation of chelosis. Retinoids have also been discovered to be useful in treating type II non-insulin dependent diabetes mellitus, fibrosis of the liver, as well as in disorders of ectopic bone formation such as cardiovascular calcification and muscle tissue calcification.

This invention also relates to a pharmaceutical formulation comprising one or more compounds as described herein in a mixture with pharmaceutically acceptable excipient, said formulation being adapted for administration to a mammal, including human to treat or alleviate the conditions which are described above as treatable by retinoids, or which are controlled by or responsive to the organism's native RA. These formulations can also be co-administered with retinoids to enhance or prolong the effects of medications containing retinoids or of the organism's native RA.

Compounds of embodiments of this invention may be administered topically or systemically, depending on such considerations as: the condition to be treated; need for site-specific treatment; quantity of drug to be administered; and other considerations. For example, in the treatment of dermatoses, it generally is preferable to administer the drug topically. Although for treatment of severe acne or psoriasis, oral administration may also be used. Any common topical formulation such as a solution, suspension, gel, ointment, or salve and the like may be used. Preparations of such topical formulations are well described in the art of pharmaceutical formulations as exemplified by Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like, or as syrup or elixir suitable for oral administration. For intravenous or Intraperitoneal administration, the compound will be prepared as a solution or suspension capable of being administered by injection. In certain cases, it may be useful to formulate these compounds in suppository form or as extended release formulation for deposit under the skin or intramuscular injection.

Other medications can be added to such topical formulation for such secondary purposes as treating skin dryness, providing protection against light, other medications for treating dermatoses, treating or preventing infection, reducing irritation, inflammation and the like.

Treatment of dermatoses or any other indications known or discovered to be susceptible to treatment by retinoid acid-like compounds, or to control by naturally occurring retinoic acid will be effected by administration of the therapeutically effective dose of one or more compounds of embodiments of the present invention. A therapeutic concentration is that concentration which prevents, treats, ameliorates, reduces symptoms, delays onset, or slows or prevents proliferation of a disease or condition. In certain embodiments, the compound may be used in a prophylactic manner to prevent onset of a particular condition.

A useful therapeutic or prophylactic concentration will vary from condition to condition and in certain cases may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in treatment of, for example, acne, or similar dermatoses that a formulation between 0.01 milligrams and 1 mg per mL will constitute a therapeutically effective concentration for topical application. If administered systemically, an amount between 0.01 and 5 mg per kg body weight per day would be expected to effect a therapeutic result in the treatment of many diseases for which these compounds are useful.

In some applications, CYP26 inhibitory compounds of the invention may be co-administered with formulations of retinoids.

The following working examples further illustrate the invention and are not intended to be limiting in any respect.

EXAMPLES

Example 1. Synthesis of Compounds of Formula (1)

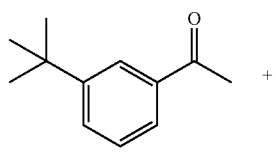

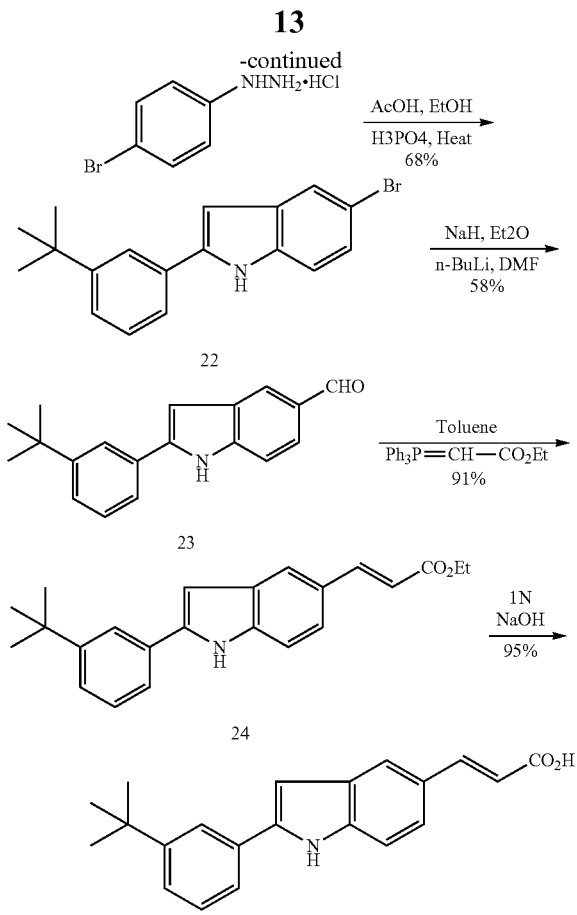

The above reaction scheme shows a synthetic pathway to synthesis of a compound of Formula (1). Compound 026 was a yellow powder that was characterized by NMR, MS, and HPLC as follows. $^1$H NMR δ (CDCl$_3$, 500 MHz): 1.3 (s, 9H), 6.43 (d, 1H), 6.85 (s, 1H), 7.26 (s, 2H), 7.40 (m, 5H), 7.68 (s, 1H), 7.82 (s, 1H), 7.93 (d, 2H), 8.50 (br s, 1H) ppm. Molecular Weight: 319.40, Formula: C$_{21}$H$_{21}$NO$_2$. Purity (HPLC): >98% (HPLC details: 90:10 MeCN:H$_2$O, 0.5 mg/mL, 254 nm; 1 mL/min.

Example 2. Retinold Activity Assays

This retinoid activity assay measures the ability of test compounds to induce expression of a transiently transfected RA sensitive reporter construct. In this assay, MCF-7 cells are transfected with a construct comprising an upstream promoter of the CYP26A1 gene containing 2 RA response elements driving expression of firefly luciferase (pCYP26A1-luc). Since CYP26A1 is highly inducible by RA in these cells, this construct serves as a sensitive reporter of retinod-like transcriptional activity.

MCF-7 cells were maintained in a RPMI-1640 medium containing 10% FBS. Exponentially growing cells were harvested by incubation in trypsin. Cells were then collected and plated in 24-well plates at 50,000 cells/well. Once cells reached 80-90% confluence (e.g., the next day), cells were transfected with two plasmids. The first plasmid was CYP26A1-luc construct (375 ng). The second plasmid was a control plasmid comprising the Renilla luciferase gene driven by constitutive thymidine kinase promoter (pRL-tk) (25 ng). Transfection was performed using FuGene 6 transfection reagent (Promega) with a 1:3 ratio of DNA:FuGene. 24 hours after transfection, cells were treated with test compounds diluted in DMSO in triplicate at 0.1, 1 and 10 μM final concentrations. As a positive control for reporter activation, cells were also treated with RA diluted in DMSO at the same concentrations listed above. DMSO treatment alone served as a negative control. After 24 hours of treatment, cells were harvested in passive lysis buffer (Promega) and luciferase activity in cell lysates were read using a luminometer. Data are expressed as the activity of firefly luciferase relative to Renilla luciferase (see Tables 3-5). For CYP26A1 inhibitor compounds, no activation of the reporter was detected, while the related retinoid-like compound induces luciferase expression.

Additionally, for some compounds of particular interest, a second assay is performed to measure expression of endogenous RA target genes after treatment with test compounds in MCF-7 cells. Exponentially growing MCF-7 cells were treated with trypsin, collected and plated into 6-well culture dishes at 300,000 cells per well. Once cells reached confluency, they were treated with test compounds diluted in DMSO to a final concentration of 1 μM. As a positive control, cells were also treated with RA at 1 μM final concentration. After 24 hours of treatment, RNA was harvested using TRI reagent (available from Sigma-Aldrich, Oakville, Canada). cDNA was synthesized from 2 μg of total RNA using Superscript III cDNA synthesis kit with random priming (kit available from Life Technologies, Burlington, ON, Canada). Analysis of expression of a RA inducible CYP26A1 gene was quantified by qPCR normalized against expression of PMM2 with Sybr Select Master Mix (Life Technologies) and gene specific primers in a two-step thermal cycling reaction. Importantly, compounds that have inhibitory activity towards CYP26B1 did not significantly induce expression of RA target genes when given alone, indicating a lack of retinoid-like activity.

Example 3. Enhancement of RA Activity Assay

An RA activity assay was used to measure the ability of compounds that inhibit CYP26 to enhance activity of RA, for example, by limiting its catabolism. This assay measured expression of endogenous RA target genes in MCF-7 cells that have been treated with RA and a compound of interest. A compound that inhibits CYP26 activity will have the effect of prolonging the induction of RA target genes in response to RA.

Figure 3:
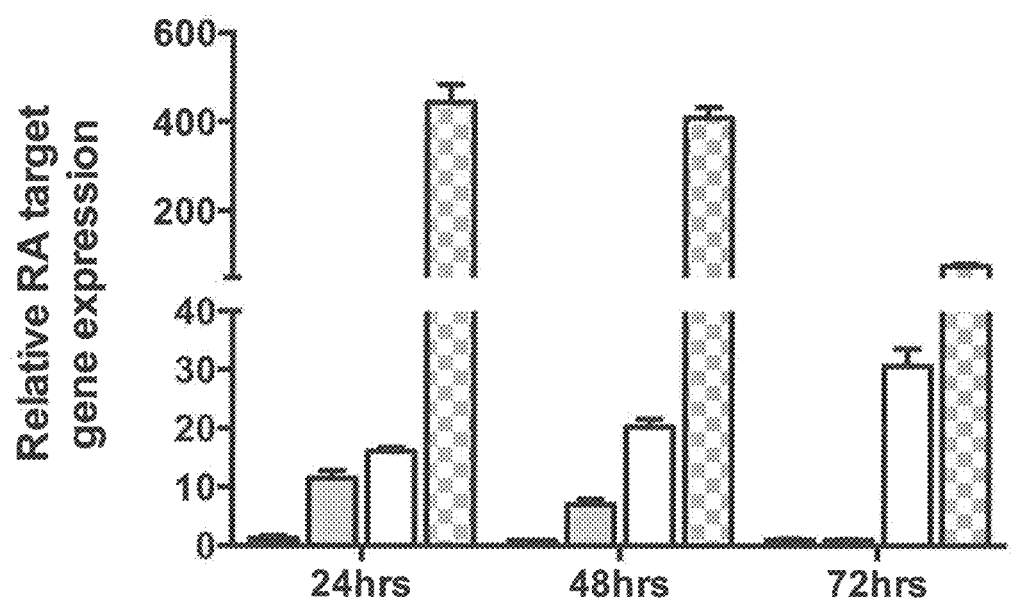
FIG. 3 shows a bar graph of QPCR analysis of CYP26A1 expression in MCF-7 cells treated with either vehicle (DMSO, black bars), 0.1 µM RA (gray bars), 1 µM compound 026 (white bars) or 0.1 µM RA plus 1 µM compound 026 (checkered bars) for 24, 48 or 72 hours.

Exponentially growing MCF-7 cells were treated with trypsin, collected and plated into 6-well culture dishes at 300,000 cells per well. Once cells had reached confluency, they were treated with CYP26 inhibitor test compounds or with ketoconazole (a non-selective CYP inhibitor) at a final concentration of 1 μM, or an equal volume of DMSO as a control. RA was also added at a final concentration of 1 μM. RNA was harvested using Trizol reagent after 24, 48, and 72 hours of treatment. cDNA was synthesized from 2 μg of total RNA using Superscript III cDNA synthesis kit with random priming (available from Life Technologies, Burlington, ON, Canada). Analysis of expression of the RA inducible CYP26A1 gene was quantified by qPCR normalized against expression of PMM2 with Sybr Select Master Mix (Life Technologies) and gene specific primers in a two-step thermal cycling reaction. Data is provided for a CYP26B1 selective inhibitor, which enhances the induction of CYP26A1. See FIG. 3 for compound 026 enhancement of RA signaling in MCF-7 cells.

Example 4. Cell-Based Inhibitor Assay

CYP26A1 or CYP26B1 stably transfected HeLa cells were maintained in Minimum Essential Medium (MEM)

containing 10% fetal bovine serum (FBS) and 100 µg/mL hygromycin. Exponentially growing cells were harvested by incubation in trypsin. Cells were then collected and re-plated in 48-well culture plates at $5 \times 10^5$ cells in 0.2 mL of culture medium containing 0.05 µCi [$^3$H]-RA in the presence or absence of increasing concentrations of a test compound. The test compounds were diluted in dimethyl sulfoxide (DMSO) and then added in duplicate to wells at 0.01, 0.1, 1, 10 and 100 µM final concentration. As a positive control for inhibition of RA metabolism, cells were also incubated with ketoconazole at the same concentrations as above. Cells were incubated for 3 hours at 37° C. Retinoids were then extracted using the procedure of Bligh, et al., (1959), Canadian Journal of Biochemistry 37, 911-917, which was modified by using dichloromethane instead of chloroform. Each sample's water soluble radioactivity level was quantified using a β-scintillation counter (using Ecolume scintillation fluid, available from MP Biomedicals of Solon, Ohio, USA). $IC_{50}$ values represented the concentration of inhibitor required to inhibit all trans-RA metabolism by 50%, and were derived from log transformed data. $IC_{50}$ values obtained in this assay for several preferred compounds are listed in Table 2.

Example 5. Leukemia Cell Differentiation Analysis by FACS

Many human non-APL AML cell lines are sensitive to RA-induced differentiation. However, co-culture of leukemic cells with bone marrow stromal cells can block this effect of RA. This assay tests the ability of CYP26 inhibitor compounds to overcome the protective effect that stromal cells have on leukemic cell differentiation. For these experiments, OP9 mouse bone marrow stromal cells are grown MEM-α containing 20% FBS, in 24 well plates until a cell monolayer is formed. OP9 cells are then irradiated (15Gy) using a GammaCell 20 cesium-137 source (located at Queen's University) in order to induce growth arrest. Leukemic cells are then added to the irradiated monolayers, or control wells without OP9 cells. AML cell lines (150,000 cells) are then plated onto OP9 monolayers in their appropriated growth medium; THP-1 RPMI-1640 medium containing 10% FBS; MDSL, RPMI-1640 medium containing 10% FBS and 10 ng/ml recombinant human IL-3; Kasumi-1, RPMI-1640 containing 20% FBS; MV4-11, IMDM containing 10% FBS. Cells are then treated for 72 hours with DMSO (vehicle control), RA (0.1 µM for THP-1 and MV4-11 cells, and 1 µM for Kasumi-1 cells), test CYP26 inhibitor compound, or the combination of RA and inhibitor compound. After the treatment period, leukemic cells are collected and stained with fluorophore labeled antibodies against cell surface antigens indicative of myeloid differentiation (PE-CD11b), or of stem cell populations (FITC-CD34, PE-CD38); all antibodies are available from BD Biosciences. Stained cells are then sorted by FACS in a BD FACS Aria 3 flow cytometer (Queen's University) using FACS Diva software, to assess percentage of cells that are CD11b$^+$, the relative expression levels of CD11b (by median fluorescence intensity—MFI), or percentage of CD34$^+$ CD38$^-$ leukemic stem cells (LSCs). Results are typically presented as the average of triplicates.

Example 6. Leukemia Cell Apoptosis

RA can also induce apoptosis is a variety of cell types, including AML cells. This experiment tests CYP26 inhibitor compounds for their ability to rescue RA-induced apoptosis in the presence of bone marrow stromal cells. For these experiments MV4-11 AML cells are plated as above, in the presence and absence of stromal monolayers. Cells are then treated for 48 hours with RA (0.1 µM). After the treatment period, cells are stained with a FITC-labeled annexin V antibody (available from Thermofisher Scientific), which binds to the surface of apoptotic cells. Cells are then sorted by FACS in a as above and data are expressed as percentage of annexin V$^+$ (apoptotic) cells.

Example 7. Leukemia Cell Colony Formation

This experiment is used to test the long-term proliferative ability of hematopoietic stem and progenitor cells as well as leukemic stem cells. Colony forming ability in long term cultures is indicative of stem/progenitor cell activity. Therefore leukemic cells treated with RA and/or CYP26 inhibitor in the presence of bone marrow stroma were tested for colony forming capacity as a measure of the effects on leukemic stem cells. For these experiments, bone marrow stromal and leukemic cell co-cultures are prepared as described above and treated with RA and/or CYP26 inhibitor compound for 72 hours. After the treatment period, leukemic cells are collected and re-plated in semi-solid methylcellulose medium to assess colony forming ability. 500 leukemic cells are plated per dish in 35 mm plates in 1.1 ml of MethoCult (available from STEMCELL Technologies, Vancouver, Canada). Triplicate plates are prepared per treatment, and cultures are grown for 14-16 days in a $CO_2$ incubator. After the culture period colonies are counted under a dissecting microscope.

Example 8. Osteoblast Cell Differentiation

RA has been shown to impact bone formation by blocking different stages of bone cell (chondrocyte/osteoblast) differentiation. These experiments are used to test the ability of CYP26 inhibitors to reduce or block osteoblast differentiation in vitro using a cell culture model. MC3T3-E1 mouse calvarias pre-osteoblasts (available from the American Type Culture Collection) were cultured in MEM-α without ascorbic acid. To induce osteoblast differentiation and matrix mineralization, cells are switched to medium containing ascorbic acid (50 µg/ml) and phosphate (10 mM β-glycerophosphate) and cultured for up to 21 days while changing media every 2-3 days. Cells are also treated with varying concentrations of RA or CYP26 inhibitor compound to assess effects on osteoblast differentiation. At the end of the treatment period, cells in 24-well plates and fixed in 70% ethanol, and stained with Alizarin red (40 mM pH 4.2) to visualize calcified extracellular matrix, indicative of osteoblast differentiation. Stained wells were photographed under a Leica MZ9$_5$ dissecting microscope. Other cells grown in 6 well plates are used for RNA extraction, and qPCR analysis of bone differentiation markers and RA target genes.

Example 9. RA Metabolism by Cultured Bone Marrow Stromal Cells and Osteoblasts

These experiments are to assess the ability of primary cells, or cell lines to metabolize RA, and to determine the effect of inhibition of CYP26A1 or CYP26B1 on this ability. For these experiments, cells are plated into 48-well plates and treated with a radiolabeled ($^3$H) RA. The extent of conversion of this labeled RA to water soluble metabolites is determined as above for in the cell-based inhibitor assay. Primary human bone marrow stromal cells (available from Lonza) were cultured in MyeloCult (available from Stem Cell Technologies, Vancouver, Canada). Mouse OP9 bone marrow stromal cells and MC3T3 pre-osteoblasts were cultured as above. Cells are plated in the appropriate culture medium and allowed to form a monolayer. Cells are then pre-treated with either DMSO (vehicle control) or RA (1 µM) for 24 hours to induce CYP26 expression. Vehicle, and RA induced cells are then exposed to $^3$H-RA in the presence or absence of test CYP26 inhibitor to examine the effects on RA metabolism. Cells are incubated for 3 hours with labeled RA, and metabolites extracted and analyzed as above.

Example 10. Induction of RA Activity in Mouse Bone Marrow

Human and mouse bone marrow stromal cells express CYP26 enzymes and Cyp26B1 is highly inducible by RA in these cells. This experiment tests whether exposure of bone marrow to a CYP26 inhibitor is sufficient to raise RA levels in the bone marrow and induce RA-target genes. Mice (8-12 week old) were given intravenous injections (tall vein) on two consecutive days (once per day) of CYP26 inhibitor compound dissolved in 0.9% sodium chloride/0.1% DMSO. Animals were given a dose of 40 µg/kg of inhibitor, or an equal volume of vehicle alone. The morning after the second injection, animals were sacrificed, and bone marrow mononuclear cells were harvested from femurs using Lympholyte-mammal reagent (available from Cedarlane, Burlington, Canada). RNA was then extracted from isolated cells, and RA target gene expression assessed by qPCR.

Example 11. Compound Effects in a Mouse Model of Acne

Retinoids have been shown to be useful in treating a variety of skin diseases in humans including acne. These experiments test the ability of CYP26 inhibitor compounds and other retinoids for potential anti-acne efficacy in a mouse model of acne. The rhino mouse model is a hairless mutant that develops skin lesions similar to acne, and has been used extensively as a model to assess new acne treatments, as well as in vivo activity of retinoids. Test compounds or RA were dissolved in acetone/10% DMSO, and 0.4 ml was applied topically to the dorsal skin of animals (2 male+2 female) once a day for five days per week, for two consecutive weeks. On the day after the last treatment, animals were sacrificed and skin was collected from the treated are and processed for histology, and epidermal sheets prepared for visualization of utriculi. Histological sections were prepared by paraffin embedding of formalin fixed samples, and stained with hematoxylin and eosin. Photographs were taken under a Nikon Eclipse E600 microscope using Q Imaging software at 20× magnification. Epidermal sheets were prepared by treating skin samples for 5 days in 0.5% acetic acid at 4° C. for 5 days, after which the dermal and epidermal layers were carefully separated, and the epidermis was then dehydrated with a series of ethanol treatments (70%, 80%, 90% and 100%). After overnight dehydration in 100% ethanol, epidermal layers were cleared using CitriSolv clearing agent (available from Fisher Scientific) and mounted on glass sides in permount (available from Fisher Scientific). Epidermal layers were then photographed as above.

Example 12. Detection of CYP26B by Immunohistochemistry

Human tissue samples were stained with an antibody against human CYP26B1 (available from Sigma-Aldrich, Canada). Staining was carried out using a ventana system at the Queen's Laboratory for Molecular Pathology.

EQUIVALENTS

It will be understood by those skilled in the art that this description is made with reference to certain embodiments and that it is possible to make other embodiments employing the principles of the invention which fall within its spirit and scope.

TABLE 1

Structural Formulae of Compounds described herein

| Compound identifier | Structural Formulae |
|---|---|
| 025 | 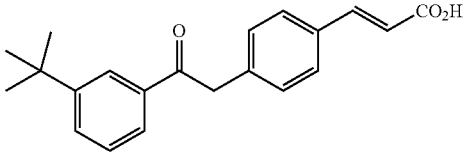 [SMILES: CC(C)(C)c1cccc(C(=O)Cc2ccc(/C=C/C(=O)O)cc2)c1] |
| 026 | 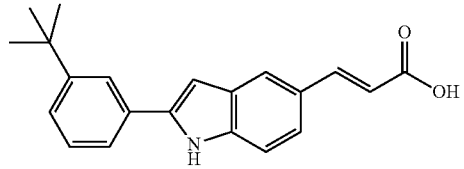 [SMILES: CC(C)(C)c1cccc(-c2cc3cc(/C=C/C(=O)O)ccc3[nH]2)c1] |
| 027 | 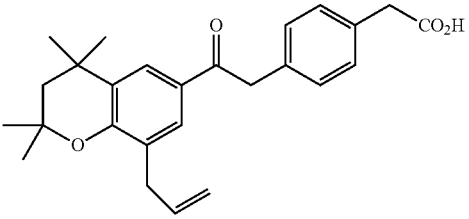 [SMILES: C=CCc1cc(C(=O)Cc2ccc(CC(=O)O)cc2)cc2c1OC(C)(C)CC2(C)C] |
| 028 | 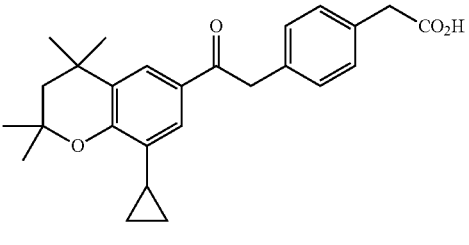 [SMILES: CC1(C)CC(C)(C)c2cc(C(=O)Cc3ccc(CC(=O)O)cc3)cc(C3CC3)c2O1] |
| 029 | 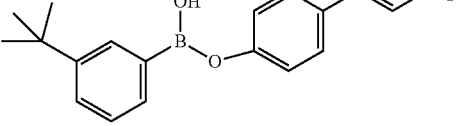 |
| 030 | 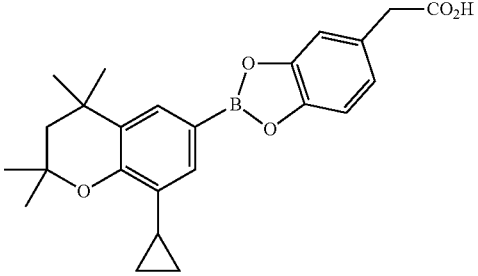 [SMILES: CC1(C)CC(C)(C)c2cc(B3Oc4ccc(CC(=O)O)cc4O3)cc(C3CC3)c2O1] |

TABLE 1-continued

Structural Formulae of Compounds described herein

| Compound identifier | Structural Formulae |
|---|---|
| 031 | (structure: 3-tert-butylphenyl-benzofuran with acrylic acid CO$_2$H) |
| 032 | (structure: 3-tert-butylphenyl-benzofuran with CH$_2$CO$_2$H) |
| 033 | (structure: tetramethylchroman-benzofuran with CH$_2$CO$_2$H and cyclopropyl) |
| 034 | (structure: tert-butyl-methylphenyl-indole with acrylic acid COOH) |

TABLE 2

CYP26 inhibitory activities of various compounds of Formula (1)

| Compound | CYP26A1 IC$_{50}$ (μM) | Rel. to keto | CYP26B1 IC$_{50}$ (μM) | Rel. to keto |
|---|---|---|---|---|
| 025 | 45.6 | 21.7 | 17.9 | 4.2 |
| 026 | 7 | 4.4 | 0.2 | 0.02 |
| 027 | 8.6 | 1.2 | 8.8 | 0.9 |
| 028 | >1000 | | >1000 | |
| 029 | n.d. | | 54.9 | 5.7 |
| 030 | 31.5 | 20 | 88.1 | 9.2 |
| 031 | n.d | | 18.3 | 2 |
| 032 | 8.6 | 1.2 | 2.3 | 0.3 |
| 033 | n.d | | n.d | |
| 034 | 9.6 | 1.9 | 0.5 | 0.2 |

TABLE 3

Relative luciferase activity of Cyp26a1-luc construct in MCF-7 cells treated with compounds 025, 027, and 028 compared with RA control

| Compound | Concentration (μM) | Rel. Luciferase Activity (mean) | SD |
|---|---|---|---|
| DMSO | | .0179 | .0028 |
| RA | 0.1 | .3966 | .1112 |
| | 1 | 1.0425 | .0498 |
| | 10 | 1.7598 | .1818 |

TABLE 3-continued

Relative luciferase activity of Cyp26a1-luc construct in MCF-7 cells treated with compounds 025, 027, and 028 compared with RA control

| Compound | Concentration (μM) | Rel. Luciferase Activity (mean) | SD |
|---|---|---|---|
| TST-025 | 0.1 | .0144 | .0087 |
| | 1 | .01 | .0005 |
| | 10 | .0128 | .0032 |
| TST-027 | 0.1 | .0116 | .0034 |
| | 1 | .0099 | .0037 |
| | 10 | .0121 | .0047 |
| TST-028 | 0.1 | .0165 | .0102 |
| | 1 | .0094 | .0024 |
| | 10 | .0144 | .005 |

TABLE 4

Relative luciferase activity of Cyp26a1-luc construct in MCF-7 cells treated with compounds 026, 029, and 030 compared with RA control

| Compound | Concentration (μM) | Rel. Luciferase Activity (mean) | SD |
|---|---|---|---|
| DMSO | | .0389 | .0023 |
| RA | 0.1 | .4793 | .046 |
| | 1 | .8996 | .0911 |
| | 10 | 2.1285 | .1961 |
| TST-026 | 0.1 | .0522 | .0222 |
| | 1 | .0472 | .0064 |
| | 10 | .0678 | .0068 |
| TST-029 | 0.1 | .0386 | .0037 |
| | 1 | .0384 | .0042 |
| | 10 | .0333 | .0002 |
| TST-030 | 0.1 | .0411 | .0056 |
| | 1 | .0343 | .0042 |
| | 10 | .0385 | .0032 |

TABLE 5

Relative luciferase activity of Cyp26a1-luc construct in MCF-7 cells treated with compounds 031, 032, and 033 compared with RA control

| Compound | Concentration (μM) | Rel. Luciferase Activity (mean) | SD |
|---|---|---|---|
| DMSO | | .0063 | .0021 |
| RA | 0.1 | .062 | .0062 |
| | 1 | .1643 | .0447 |
| | 10 | .2458 | .0153 |
| TST-031 | 0.1 | .0039 | .0008 |
| | 1 | .0047 | .0021 |
| | 10 | .0034 | .0007 |
| TST-032 | 0.1 | .0019 | .0005 |
| | 1 | .0015 | .0007 |
| | 10 | .0004 | .0003 |
| TST-033 | 0.1 | .0024 | .0003 |
| | 1 | .0026 | .0005 |
| | 10 | .0027 | .0007 |

We claim:

1. A method of treating a disease or condition in a mammal, comprising administering a compound of the following formula:

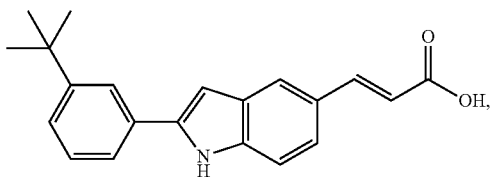

Compound 026 wherein the administering is sufficient for treating the disease or condition in the mammal, and the disease or condition is ectopic bone formation.

2. The method of claim 1, wherein the ectopic bone formation comprises cardiovascular calcification or muscle tissue calcification.

3. The method of claim 1, wherein the compound is administered as a powder, spray, pill, tablet, syrup, elixir, solution or suspension capable of being administered by injection, suppository, extended release formulation for deposit under the skin or intramuscular injection.

4. The method of claim 1, wherein the compound is included in a medicament for systemic administration in a formulation comprising between 0.01 and 5 mg per kg body weight per day.

5. The method of claim 1, wherein the compound is given in combination with a retinoid or a retinoid precursor selected from retinol, retinaldehyde, RA, or other natural or synthetic retinoids.

6. The method of claim 5, wherein the combination is provided in a tablet, capsule, injectable, or topical formulation.

7. The method of claim 1, wherein the mammal is a human.

8. The method of claim 2, wherein the ectopic bone formation is cardiovascular calcification.

9. The method of claim 2, wherein the ectopic bone formation is muscle tissue calcification.

* * * * *